United States Patent [19]

Ploetz

[11] Patent Number: 5,666,392

[45] Date of Patent: Sep. 9, 1997

[54] X-RAY DIAGNOSTIC INSTALLATION WITH A POSITIONING APPARATUS FOR A RADIATION EMITTER AND A RADIATION RECEIVER

[75] Inventor: Josef Ploetz, Bensheim, Germany

[73] Assignee: Siemens Aktiengesellschaft, Munich, Germany

[21] Appl. No.: 711,023

[22] Filed: Sep. 9, 1996

[30] Foreign Application Priority Data

Sep. 12, 1995 [DE] Germany ................ 195 33 716.6

[51] Int. Cl.⁶ ............................................. A61B 6/14
[52] U.S. Cl. ............................. 378/39; 378/38; 378/196
[58] Field of Search .............................. 378/38, 39, 40, 378/189, 191, 193, 197, 196

[56] References Cited

U.S. PATENT DOCUMENTS 5,355,398  10/1994  Nakano et al. ................ 378/38
5,371,775  12/1994  Kanerva et al. ............... 378/38

FOREIGN PATENT DOCUMENTS

OS 44 14 689  11/1995  Germany.

OTHER PUBLICATIONS

"Simplified and Standardized Bisecting–Angle Technic for Dental Radiography," Updegrave, Journal of the American Dental Association, No. 75 (1967) pp. 1361–1368 no month.

*Primary Examiner*—Don Wong
*Attorney, Agent, or Firm*—Hill, Steadman & Simpson

[57] ABSTRACT

In an X-ray diagnostic installation having a positioning arrangement for a radiation emitter and for a radiation receiver, a first positioning apparatus is provided for the radiation emitter and a second positioning apparatus is provided for the radiation receiver. The positioning apparatuses have a common reference axis. By a coupling the radiation emitter to the first positioning apparatus, the reference beam of a beam of radiation emitted by the radiation emitter intersects the common reference axis at an acute angle, and strikes the radiation receiver at least approximately centrally.

7 Claims, 2 Drawing Sheets

X-RAY DIAGNOSTIC INSTALLATION WITH A POSITIONING APPARATUS FOR A RADIATION EMITTER AND A RADIATION RECEIVER

BACKGROUND OF THE INVENTION

1. Field of the Invention

The present invention is directed to an X-ray diagnostic installation with a positioning apparatus for a radiation emitter and a radiation receiver.

2. Description of the Prior Art

In dental X-ray diagnostics, positioning apparatuses for an X-ray film are known. The X-ray film is hereby arranged in the mouth, and is oriented in relation to a source of X-ray radiation by means of the positioning apparatus. An apparatus of this type is known, for example, from the Journal of the American Dental Association (J.A.D.A.), 1967, no. 75, pp. 1361–1368, Updegrave, W. J., "Simplified and Standardized Bisecting-angle Technic for Dental Radiography." By means of this apparatus, it is intended to ensure that a beam of radiation emanating from an X-ray source strikes the film plane in as perpendicular a manner as possible. A coupling between the film holder and the X-ray source, however, is neither mentioned nor provided.

From German OS 44 14 689, an X-ray diagnostic installation with a positioning apparatus for a radiation emitter is known. By means of the coupling of the radiation emitter to this positioning apparatus, it is ensured that a reference ray of an emitted beam of radiation intersects a reference axis, which is stationary in relation to the positioning apparatus, at an acute angle α. It is further known that by coupling the radiation emitter can move to positions along a circular arc, whereby the center of the circular arc lies on the reference axis. It is further known to couple a support arm for a radiation converter onto the apparatus, which predetermines the distance to the apparatus, and thus to the focus of the radiation emitter, of a subject to be examined. The distance is chosen so that the reference ray of the beam of radiation strikes the center of the radiation converter.

SUMMARY OF THE INVENTION

An object of the present invention is to construct an X-ray diagnostic installation of the type described above such that it is suited, in particular, for the production of tomosynthesis exposures, in particular for the diagnosis of relatively small areas within larger objects, e.g., a joint of an extremity, or parts of the skull, in particular the teeth and the joints of the jaw. This apparatus should in addition be uncomplicated to handle and economical to manufacture. It should in particular be so constructed that during a dental examination the radiation receiver need not be arranged in the mouth of a patient.

The above object is achieved in accordance with the principles of the present invention in an X-ray diagnostic installation having a first positioning apparatus for a radiation emitter and a second positioning apparatus for a radiation receiver, the first and second positioning apparatuses being disposed at a distance from each other and having a common reference axis. The radiation emitter is coupled to the first positioning apparatus so that a reference ray of a radiation beam emitted by the radiation emitter intersects the common reference axis at an acute angle, and strikes the radiation receiver at least approximately in the center thereof. The radiation emitter and the radiation receiver can occupy respective positions along a circular arc, the center of the circular arc lying on the common reference axis.

It is an advantage of the invention that a positioning apparatus is respectively provided both for the radiation emitter and for the radiation receiver, which have a common reference axis. The distance between the radiation emitter and the radiation receiver is thereby predetermined. For the production of tomosynthesis exposures, it is advantageous if, given a coupling of the radiation emitter to the first positioning apparatus, a reference beam of a beam of radiation emitted by the radiation emitter intersects the common reference axis at an acute angle and strikes the radiation receiver at least approximately in the center. The radiation receiver can thus generate signals that are spatially resolved in directions lateral to the reference beam, so that on the basis of these signals sectional images in predetermined planes can be calculated.

DESCRIPTION OF THE PREFERRED EMBODIMENTS

Figure 1:
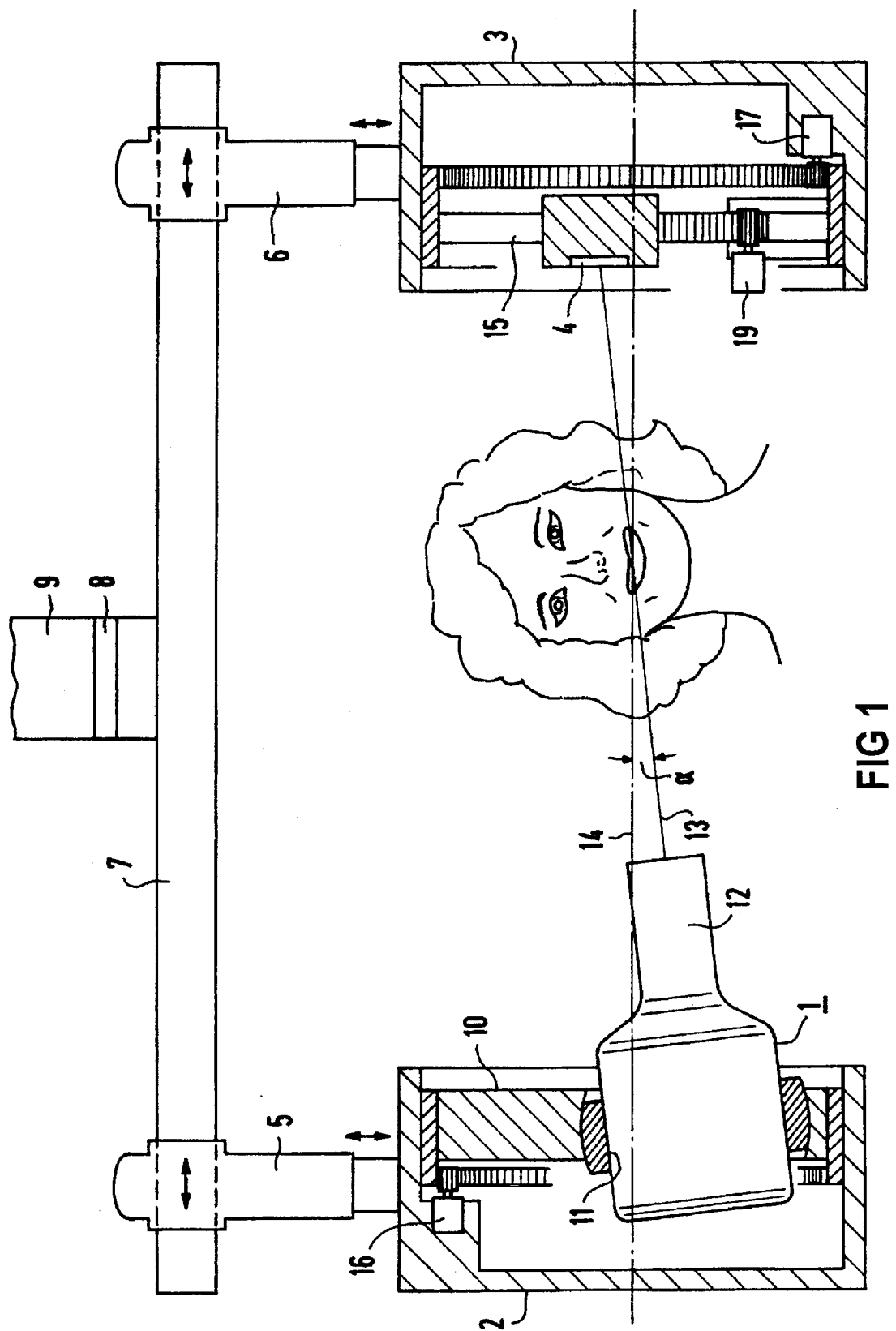
FIG. 1 shows, in a basic manner, an X-ray diagnostic installation according to the invention.

In the X-ray diagnostic installation shown in FIG. 1, a first positioning apparatus for a radiation emitter 1 is identified with the reference character 2. A second positioning apparatus 3 for a radiation receiver 4 is inventively provided. The positioning apparatuses 2 and 3 are respectively held on linkages 5 and 6, by means of which they can be adjusted with respect to height and adjusted along a support 7. The support 7 is mounted by means of a rotating joint 8 and a column 9 on the cover of a chamber. The first positioning apparatus 2 can have a disc-shaped positioning element 10, for example a wobble plate, having a recess 11 for receiving the housing or the body of the tube 12 of the radiation emitter 1. The coupling of the radiation emitter 1 to the disc-shaped positioning element 10 via the recess 11, causes a reference ray 13, e.g. the central ray, of a beam of radiation emitted by the radiation emitter 1 to intersect a common reference axis 14 of the positioning apparatuses 2 and 3 at an acute angle α. The reference axis 14 lies, for example, in the central region of the disc-shaped positioning element 10 of the first positioning apparatus 2 and in the central region of a second disc-shaped positioning element 15, on which the radiation receiver 4 is mounted. The disc-shaped positioning elements 10 and 15 are mounted on their linkages 5 and 6 so that they can be respectively adjusted about the common reference axis 14 by actuators 16 and 17. By means of a control circuit 18, explained below in FIG. 2, the radiation receiver 4 is adjusted by the actuator 17 to a position such that the reference beam 13 strikes the radiation-detecting surface of the receiver 4 at least approximately centrally.

In the exemplary embodiment, the radiation receiver 4 can be coupled with a disc-shaped positioning element 15, which can be adjusted about the reference axis 14 by an actuator 17, and which can be adjusted with regard to distance to the reference axis 14 by a further actuator 19. By controlling the actuators 16, 17 and 19, the radiation emitter 1 and the radiation receiver 4 can be moved to positions along a circular arc, and the radius of the circular arc described by the radiation receiver 4 can be varied.

The same effect can also be achieved, however, by means of an arrangement including a disc-shaped or annular element having several recesses along a circular arc, into which the body of the tube 12 can be coupled. It is then necessary, however, to provide detector elements that detect the respective position of the radiation emitter 1 and deliver a corresponding signal to a control unit for the adjustment of the radiation receiver 4. Of course, it is also possible within the scope of the invention to construct a mechanical apparatus wherein the radiation emitter 1 and the radiation receiver 4 are respectively positioned so that, given a change of position of, e.g., the radiation emitter 1, a corresponding change of location of the radiation receiver 4 ensues in such a way that the reference beam 13 intersects the common reference axis 14 at an acute angle α.

In a variant of the invention, the first and second positioning apparatuses 2 and 3 are constructed so that the distance of the radiation emitter 1 or of the radiation receiver 4 to the common reference axis 14 can be altered.

The dimensions of the radiation receiver 4 are preferably smaller than the average distance between the reference axis 14 and the reference beam 13 at the location of the radiation receiver 4 in the different positions occupied by the radiation emitter 4, with the radiation receiver 4 being positioned so that in the different positions occupied by the radiation emitter 1, the reference beam 13 respectively strikes approximately at the center of the radiation receiver 4.

Figure 2:
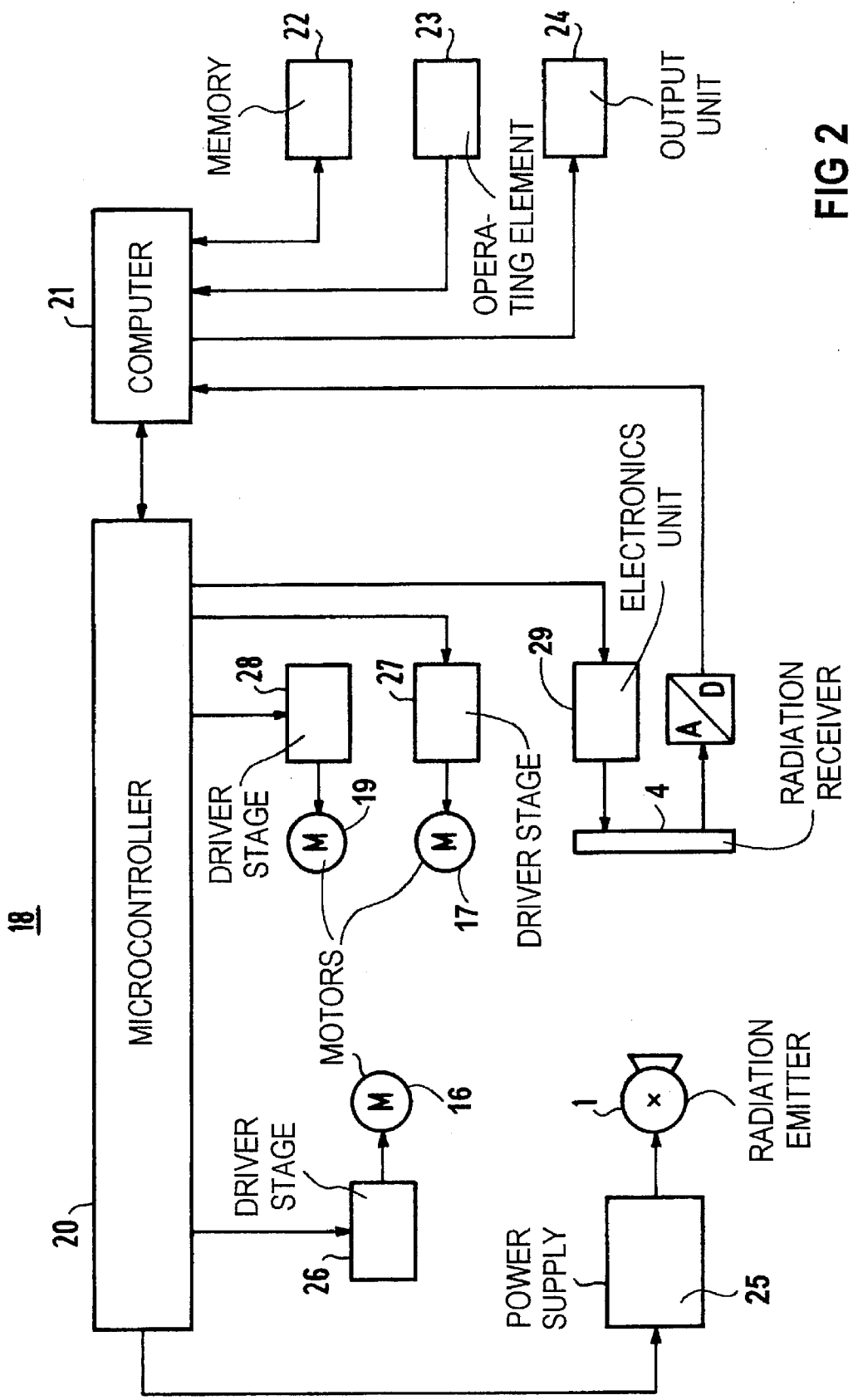
FIG. 2 is a block diagram of control components for the X-ray diagnostic installation according to FIG. 1.

FIG. 2 shows a control circuit 18 for the actuators (motors) 16, 17 and 19, which includes a microcontroller 20 and an allocated computer 21, to which is allocated a memory 22, an operating element 23 and an output unit 24. A power supply 25 for the radiation emitter 1 is driven via the microcontroller 20, the actuators 16, 17 and 19 are driven by respective driver stages 26, 27 and 28 and an electronics unit 29 for the radiation receiver 4. It is thereby possible to set the position of the radiation emitter 1 and the position of the radiation receiver 4 in a manner controlled electronically and/or through software.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray diagnostic installation comprising:

a radiation emitter which emits an X-ray beam, said X-ray beam including a reference ray;

a radiation receiver on which X-rays from said radiation emitter are incident a first positioning apparatus for said radiation emitter;

a second positioning apparatus for said radiation receiver, said second positioning apparatus being disposed a distance from said first positioning apparatus and said first and second positioning apparatuses having a common reference axis;

means for coupling said radiation emitter to said first positioning apparatus for causing said reference ray of said X-ray beam to intersect said common reference axis at an acute angle and to strike said radiation receiver approximately at a center of said radiation receiver; and said first and second positioning apparatuses comprising, in combination means for positioning said radiation emitter and said radiation receiver at respective positions along a circular arc centered on said common reference axis.

2. An X-ray diagnostic installation as claimed in claim 1 wherein said first positioning apparatus comprises means for positioning said radiation emitter at respective positions along a first circular arc and wherein said second positioning apparatus comprises means for positioning said radiation receiver at respective positions along a second circular arc having a radius which is variable independently of a radius of said first circular arc.

3. An X-ray diagnostic installation as claimed in claim 1 comprising means for mechanically coupling said first and second positioning apparatuses.

4. An X-ray diagnostic installation as claimed in claim 1 comprising means for electromechanically coupling said first and second positioning apparatuses.

5. An X-ray diagnostic installation as claimed in claim 1 further comprising control means for selecting said respective positions of said radiation emitter and said radiation receiver.

6. An X-ray diagnostic installation as claimed in claim 1 wherein said reference ray strikes said radiation receiver after passing through an examination subject disposed between said first and second positioning apparatuses, and wherein said radiation receiver comprises means for generating signals corresponding to radiation incident thereon which are spatially resolved in a direction lateral to said reference beam and a direction lateral to said reference axis.

7. An X-ray diagnostic installation as claimed in claim 1 wherein said radiation receiver has dimensions smaller than an average distance between said reference axis and said reference ray at said radiation receiver for the respective positions occupied by said radiation emitter, and wherein said second positioning apparatus comprises means for positioning said radiation receiver relative to the respective positions occupied by said radiation emitter for always causing said reference beam to strike approximately said center of said radiation receiver.

* * * * *